United States Patent [19]

Naqui et al.

[11] Patent Number: 5,155,022
[45] Date of Patent: Oct. 13, 1992

[54] ASSAY FOR LYME DISEASE

[75] Inventors: Ali Naqui, Sparks, Md.; Liane F. Gossett, Morrisville; James P. Mapes, Raleigh, both of N.C.

[73] Assignee: Becton, Dickinson and Company, Franklin Lakes, N.J.

[21] Appl. No.: 652,681

[22] Filed: Feb. 8, 1991

[51] Int. Cl.$^5$ .......................................... G01N 33/569
[52] U.S. Cl. .................................... 435/7.32; 435/962; 435/975; 436/518; 436/530; 436/174; 436/175; 436/808; 436/810; 436/811; 436/825; 436/800; 436/829
[58] Field of Search ..................... 435/7.32, 962, 968, 435/975, 259, 810, 820; 436/518, 528, 530, 174, 800, 808, 811, 810, 829, 825

[56] References Cited

U.S. PATENT DOCUMENTS

| 4,888,276 | 12/1989 | Shelburne | 435/7.32 |
| 4,920,046 | 4/1990 | McFarland et al. | 436/518 |
| 4,978,625 | 12/1990 | Wagner et al. | 436/518 |

OTHER PUBLICATIONS

Pfister et al. J. Neurol 231:141–144 (1984).
Weber et al, Yale Journal of Biology and Medicine 57:463–471 (1984).
Ackermann et al, Yale Journal of Biology and Medicine 57:573–580 (1984).
Wilske et al, Infection 12(5):331–337 (1984).
Access ImmuroClone Lyme Disease Test package insert, Access Medical Systems, Inc.
Magnarelli et al, "Cross-reactivity of nonspecific treponemal antibody in serologic tests for Lyme Disease" J. Clin Microbiol. 28(6):1276–1279 (Jun. 1990).
Magnarelli, "Serologic Diagnosis of Lyme Disease" in Annals of the New York Academy of Sciences, vol. 539:154–161 (1988).
Russell et al., Journal of Infectious Diseases, 149, 465 (1984).
Grodzicki et al., Journal of Infectious Diseases, 157, 790 (1988).
Coleman et al., Journal of Infectious Diseases, 155,756 (1987).
Raoult et al., Journal of Clinical Microbiology, 27, 2152 (1989).
Magnarelli et al., American Journal of Empidemiology, 127, 818 (1988).
Craft et al., Journal of Infectious Diseases, 149, 789 (1984).

Primary Examiner—Esther L. Kepplinger
Assistant Examiner—Carol E. Bidwell
Attorney, Agent, or Firm—Richard E. Btown; Donna R. Fugit

[57] ABSTRACT

Diagnosis of Lyme disease by immunoassay for anti-Borrelia burgdorferi antibodies in the serum of a patient includes adsorption of crossreactive antibodies in the serum with antigen of Acinetobacter calcoaceticus or Treponema phagedensis prior to binding of anti-Borrelia antibodies to Borrelia burgdorferi antigen absorbed onto a solid support. The preferred assay is a flow-through assay using a porous membrane as the support and a dye-loaded liposome conjugated to a goat antihuman antibody for detection. The invention includes a kit of materials for performing the assay.

15 Claims, No Drawings

ASSAY FOR LYME DISEASE

BACKGROUND OF THE INVENTION

1. Field of the Invention

This invention relates to Lyme disease, and more specifically relates to an assy for serum antibodies against Lyme disease antigen in which crossreactivity of the antigen to other antibodies in the serum is reduced.

2. Background of the Invention

*Borrelia burgdorferi*, a species within the genus Borrelia and family Treponemataceae, is a tick-borne spirochete which has been identified as the causative agent of Lyme disease.

Several approaches to diagnosis of Lyme disease have been investigated. Diagnosis by histological identification of the spirochete is very difficult because the spirochete to present in tissue or body fluid in small numbers, even in many advanced cases, and isolation is even more difficult. Diagnosis by assay for Borrelia antigen is disclosed U.S. Pat. No. 4,888,276 to Shelbourne. In the Shelbourne assay, a urine sample from a patient suspected of having Lyme disease is combined with an anti-Borrelia antibody, monoclonal or polyclonal, raised against the antigen and the antigen-antibody complex is detected with an enzyme labeled antiantibody.

Most reports on diagnosis of the disease have relied on assay of serum samples for anti-Borrelia antibodies present in a patient's serum in response to infection. Several types of assays have been developed including enzyme linked immunosorbent assay (ELISA) and immunofluorescence assay (IFA).

At the present state of the art, ELISA and IFA assays of sera from patients in the early stages of the disease, some of whom may be clinically asymptomatic, is generally recognized to be unsatisfactory because of weak antibody response. Also, false positives arising from crossreactivity wit other antibodies in the serum decease the specificity of the assays. For example, Russell et al. in the *Journal of Infectious Diseases*, 149, 465 (1984) assayed sera from healthy individuals, patients with Lyme disease, and patients with other infections by ELISA and IFA and found significant crossreactivity unless sera from other treponemal-infected patients were excluded.

Likewise, Grodzicki et al. in the *Journal of Infectious Disease*, 157, 790 (1988) describes a comparative study of the effectiveness of an indirect ELISA assay and an immunoblot assay for diagnosis of early Lyme disease, and concludes that less false positives result with the immunoblot method.

Attempts to improve assays for Lyme disease by enrichment of Borrelia antigen or adsorption of the crossreacting antibodies with proteins have been reported. Thus, Coleman et al., in the *Journal of Infectious Diseases*, 155, 756 (1987) shows that assay for Lyme disease by ELISA is improved by removal of the outer envelope fraction of the spirochete, electrophoresis and Western blotting of the residue to isolate a flagellin-enriched protein fraction and use of this material as the capture antigen. Fawcett et al. absorbs crossreacting antibodies with *E. coli* to reduce nonspecific binding and false positives.

Raout et al., in the *Journal of Clinicial Microbiology*, 27, 2152 (1989) discloses reduction in crossreactivity of sera positive for leptospirosis, syphilis or human immunodeficiency virus in the micro IFA test. The Raout et al. method includes adsorption of crossreacting antibodies with an ultrasonicate of Reiter treponemes at 37° C. for 60 minutes. On the other hand, Magnarelli et al. in the *American Journal of Epidemiology*, 127, 818, (1988) report that, to date there has been limited success in efforts to increase the specificity of ELISA for Lyme disease by adsorption with *Borrelia hermsii* or Reiter treponemes.

Craft et al., in the *Journal of Infectious Diseases*, 149, 789 (1984) compares ELISA and IFA assays which include 90 minute preadsorption at 23° C. Craft et al. concludes that ELISA is more sensitive and specific than IFA, and ELISA without preadsorption of crossreacting antibodies is the best diagnostic test of Lyme disease.

A commercial Lyme disease assay kit sold by Zeus Scientific Inc. Raritan, N.J., utilizes the IFA technique and is claimed to be useful for confirmation of Lyme disease in its later stages. A commercial ELISA kit sold under the trade name IMMUNOCLONE ® by Access Medical Systems is claimed to be more accurate than the leading commercially available laboratory methods.

In a copending application of common assignee herewith, a method of assay for Lyme disease is disclosed in which Lyme disease capture antigen is denatured to improve assay spcificity.

Lyme disease was first identified in 1975, and today is well-recognized as a growing menace. In spite of extensive research, no satisfactory assay for the disease has yet been advanced, and diagnosis still relies heavily on clinical observations. There is thus a need for a rapid and reliable assay of high sensitivity and specificity. The present invention is directed to fulfulling this need.

SUMMARY OF THE INVENTION

An assay for Lyme disease includes binding of anti-*Borrelia burgdorferi* antibodies (hereinafter referred to as analyte antibodies) to *Borrelia burgdorferi* antigen (hereinafter referred to as capture antigen) on a solid phase. A serum sample from a patient suspected of having Lyme disease is mixed with an antigen (hereinafter referred to as absorbing antigen) of *Acinetobacter calcoaceticus* (hereinafter *A. cal.*) or *Treponema phagedensis* (also known as *Treponema reiteri* and by the trivial name *Reiter treonemes;* hereinafter *T. phag.*). Other antibodies in the serum (hereinafter called crossreactive antibodies) bind selectively to the absorbing antigen. The mixture is added to a solid support coated with capture antigen to cause binding between capture antigen and the analyte antibodies captured thereon is contacted with a tracer including a detection antibody labeled with a dye. Binding of the detection antibody to the analtye antibody results in adherence of the dye of the solid support. Detection of the dye is a positive assay for Lyme disease.

The absorbing antigen may be mixed with the serum sample in the form of the whole *A. cal.* or *T. phag.* microorganism or after disruption of the microorganism.

In a preferred assay, the solid support is a porous membrane coated with capture antigen and the assay is performed by flow through assay in which liquids used as vehicles for the assay reagents or for wash steps pass through the membrane by capillary action induced by absorbent material under the membrane.

In the most preferred assay, the tracer includes an absorbing dye encapsulated in a liposome conjugated to antihuman immunoglobulin detection antibody.

The invention includes a kit of materials for performing the assay.

Thus, in accordance with present invention, it has been discovered that adsorption of crossreactive antibodies with antigen from particular disrupted microorganisms occurs instantaneously at room temperature to provide an assay of high specificity and sensitivity when performed by flow through format with a tracer including a dye loaded liposome. It is believed that the liposome, because it carries a multiplicity of dye molecules for each detection antibody, provides many labeled detection molecules for each analyte antibody which is captured by the capture antigen. A detectable level of color is thereby achieved even when the serum has a low analyte antibody titer.

The assay of the invnetion requires only 90 seconds to complete and has no time-critical steps as compared to 6.5 minutes and three time-critical steps for IMMUNO-CLONE.TM. Accordingly, many more assays may be performed in a short time by relatively unskilled technicians in a laboratory setting, a physician's office or even in the home.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

One aspect of the invention is an improved assay for detection of Lyme disease. The assay detects the presence of analyte antibodies to the spirochete, Borrelia burgdorferi in a patient's serum. In accordance with the invention, crossreactive antibodies in the patient's serum which may bind nonspecifically to Borrelia burgdorferi capture antigen are absorbed onto absorbing antigen of particular microorganisms and thereby prevented from crossreacting with the capture antigen.

The preferred assay of the invention is a solid phase assay in which capture antigen absorbed on a solid support serves to capture analyte antibodies in the patient's serum. Any conventional solid support as known in the art may be used, as, for example, the wells of a microtiter plate, a dipstick or the inside wall of a tube or cuvette. The preferred assay technique is flow-through assay in which the solid support is a porous membrane. The membrane may be positioned in any suitable assay device adapted for flow-through assay as known in the art. In preferred devices, flow of assay liquids is promoted by capillary action induced by a pad of absorbent material adjacent the membrane, and the membrane and absorbent pad are mounted in a suitable housing. Membrane flow-through assay and various devices therefore have been disclosed and several devices are commercially available.

The porous membrane may be of any material which does not interfere in any way with any other component or step of the assay. Suitable membranes are, for example, of glass fiber, polyvinylidene difluoride, polycarbonate, nitrocellulose and nylon. Such membranes are well-known in the art and many are commercially available from suppliers such as Pall (East Hills, N.Y.), Millipore (Bedford, Ma.) and Schleicher and Schuell (Keene, N.H.).

The capture antigen may be prepared by any procedure as known in the art. In one suitable procedure, the spirochete, available from the American Type Culture Collection, Rockville, Md., may be grown in a suitable medium, harvested, and suspended in a suitable diluent such as phosphate buffered saline (PBS). After disruption of the cells with a detergent or preferably by sonication, the mixture is cnetrifuged and the supernatant diluted with PBS to give a stock solution containing a final desired protein concentration, preferably about 1 to 10 mg/ml.

Absorption of the capture antigen onto the membrane is wholly conventional and may be performed by covalent attachment or preferably by physical absorption. In the latter technique, a suitable quantity of the antigen stock, generally about 300 $\mu$l, may be spotted on the membrane and the liquid phase allowed to pass through by capillary action. As the liquid flows through, the antigen is absorbed on the membrane.

After absorption of the capture antigen, the membrane may be further coated with an inert protein to fill any binding sites on the membrane not occupied by the capture antigen. (In the present disclosure, the term inert protein means a protein which is immunologically unreactive toward any other component of the assay and which does not substantially bind nonspecifically to other proteins in the assay medium, with the understanding that the inert protein may well be immunologically reactive toward other materials which are not part of the assay of the invention.) Representative nonlimiting examples of suitable inert proteins are casein and albumin, although others will be evident to those skilled in the art.

A sample of plasma, whole blood or preferably serum from a patient suspected of having Lyme disease may be brought into contact with an absorbing antigen of a particular microorganism which selectively and instantaneously absorbs crossreactive antibodies in the serum. Suitable microorganisms are A. cal. and T. phag. The organism may be broken apart by a conventional lysing procedure such as with a detergent or surfactant, or by a physical treatment, such as with heat or by sonication. Alternatively, the antigen may be in the form of a whole cell, preferably heat killed. Most preferably, the absorbing antigen is a lyophilized preparation of heat disrupted T. phag. which may be used after reconstitution with a buffer such as Tris or PBS. The absorbing reagent is available from BBL Microbiology Systems, division of Becton, Dickinson and Company, Cockeysville, Md., under the name FTA-ABS Test Sorbent.

The reconstituted absorbing antigen may contain about 0.01 to 20, preferably about 1.0 to 5.0 mg/ml of protein. Preferably a volume, about 50 to 500 $\mu$l, sufficient to contain about 0.25 to 2.5, preferably about 0.5 to 1.0 mg of absorbing protein is mixed with about 10 to 100, preferably about 25 $\mu$l of serum. Adsorption takes place immediately upon mixing.

When the mixture of serum and absorbing antigen is passed through the membrane, analyte antibodies present in the serum bind to the capture antigen on the membrane. Crossreactive antibodies in the serum, on the other hand, having been preabsorbed onto the absorbing protein, pass through the membrane.

Analyte antibodies captured on the membrane are detected by passing a tracer containing a label through the membrane. A preferred tracer is a dye-labeled detection antibody which binds with the analyte antibody. In the most preferred tracer, the detection antibody is a goat anti-human antibody raised against human immunoglobulin by wholly conventional procedures.

Suitable dyes are absorbing dyes for fluorescent dyes, and the invention contemplates any dye known in the art as a label in immunoassay. Representative nonlimiting dyes are fluorescein, alizarin red, congo red, brilliant green, toluidine blue and the like. The preferred dye is sulforhodamine B.

In a preferred tracer, the dye is occluded in a particulate medium. As known in the art, the occluding medium may be a polymeric microparticle or it may be any one of the wide variety of sacs known in the art. A particularly useful type of sac is a vesicle, most preferably a liposome.

Liposomes may be prepared by any one of a wide variety of procedures. Thus, for example, a liposome may be prepared by a reverse emulsion technique wherein there is provided a water-in-oil emulsion containing the materials for forming the liposome (generally phospholipids), as well as the dye to be occluded. Evaporation of the solvent gives a gel-like mixture which is converted to the liposome having the dye occluded therein by agitation, sonication or addition of the gel-like mixture to water.

In accordance with the invention, the liposome may be of any shape, but preferably is substantially spherical. The preferred liposomes may be from about 0.01 to 1 $\mu$m in diameter, most preferably from about 0.2 to 0.4 $\mu$m. Liposomes within the desired size range may conveniently be obtained by passage of liposomes of mixed sizes through filters of appropriate pore size.

The liposome may be conjugated to the detection antibody by a variety of conventional procedures, preferably by covalent coupling. Covalent coupling may be performed directly or by way of a spacer compound having two reactive functional groups, one of which is capable of reacting or being linked to a functional group of the detection antibody portion of the tracer, and the other of which is capable of reacting or being linked to a functional group on the liposome. In another technique, the detection antibody may be coupled to one of the materials used in forming the liposome. These procedures are generally well-known in the art, and no further details in this respect are deemed necessary for a complete understanding of the invention.

When the tracer passes through the membrane, the detection antibody portion binds to analyte antibody captured on the membrane as described above. The dye-loaded liposome is thereby affixed to the membrane and detection of the dye is indicative of the presence of analyte antibodies in the patient's serum. Detection of the dye is by any conventional method dependent on the nature of the dye. Thus, if the dye is a fluorescent, dye, fluorescence from the membrane is detected. If the dye is an absorbing dye, a colored spot on the membrane is detected. In the most preferred embodiment of the invention, the dye is sulforhodamine B and the development of a pink or red color on the membranes is indicative of a Lyme disease infection in the patient.

Another aspect of the invention is a kit of materials useful for performing the assay of the invention. The kit may include a solid support having affixed thereto a *Borrelia burgdorferi* capture antigen. Another component of the kit is an absorbing antigen of a microorganism which adsorbs crossreactive antibodies in a serum sample to be assayed. The kit may be configured to include the absorbing antigen in the form of the intact microorganism or as a disrupted microorganism to be reconstituted with a buffer prior to use. The kit may also include a tracer having a dye and a detection antibody which binds to the analyte antibody.

In a preferred kit, the solid support is a porous membrane which is mounted over an absorbent pad in an enclosure having access to the membrane for application of assay reagents and the dye is encapsulated in a liposome conjugated to the detection antibody.

The kit may optionally contain various buffers, vials, tubes, droppers and the like useful for performing the assay, and may include known Lyme positive and negative serum samples as standards for comparison with the unknown.

The following examples are provided to further describe the invention but are not to be considered as limitative of the invention.

EXAMPLE I

Assay for Antibody to *Borrelia burgdorferi*

I. Materials

A. Preparation of Antigen Stock

An antigen stock was prepared by sonication and subsequent centrifugation of *Borrelia borgdorferi* (ATCC #B31, 35210), grown in BSK II media (ATCC 190 1316). Once produced, this antigen was diluted in Dulbecco's Phosphate Buffered Saline (D-PBS) (Gibco, CAT #310-4040AC Grand Island, N.Y.), to a final protein concentration of 5 mg/ml.

B. Assay Device

Top Layer —
Five micron pore size nitrocellulose membrane (MSI, Westboro, Ma.)
Next Layer —
Non-woven rayon sheet (Schleicher and Schuell, Keene, N.H. 190 5-S).
Bottom Layer —
Cellulose absorbent pads (2) (Filtration Sciences, Mount Springs, Pa. #ED 320-200).
These layers were encased in a plastic holder which included a receiving well formed above the top layer. All reagents were added through the receiving well.

C. Serum Diluent with *T. phag.* Adsorbent

One vial of FTA-ABS Test Sorbent was reconstituted with 5 ml of HPLC grade water. The reconstituted sorbent was diluted with 15 ml of Tris buffer (100 mM Tris containing 04% w/v sodium azide) and 10 ml of HPLC grade water. FTA-ABS test sorbent is a dehydrated preparation of disrupted *T. phag.* organisms and rabbit serum.

D. Serum Diluent with *A. cal. var. antiratus* Adsorbent

Prepared by sonication and subsequent centrifugation of *A. cal* (ATCC #15308) and diluted in D-PBS to a final protein concentration of 0.4 mg/ml.

E. Detection reagent:

Liposomes containing encapsulated sulforhodamine B and conjugated to goat anti-human immunoglobulin in the following buffer: 50 mM 3-(N-morpholino)-2-hydroxypropane, 20 mM ethylene-diaminetetraacetic acid disodium salt, 0.05% v/v dimethyl sulfoxide, 0.2% w/v sodium azide, 1.25% w/v glycerol, 0.8% bovine serum albumin (BSA), pH 7.4.

II. Assay Procedure

The antigen stock (300 μl) was spotted onto the membrane in the shape of a triangle. In the center of this antigen triangle, 1 μl of human immunoglobin G (IgG) (62.5 ng/μl) was spotted to act as a control spot. The membrane was then placed on an aspirator, and 200 μl of blocking buffer (50 mM Tris, 3% w/v BSA, 10% w/v sucrose, 0.02% w/v sodium azide, pH 8.0) was added. The membrane was then air dried at 45° C. for 15 minutes, followed by a room temperature incubation in >50% relative humidity for 20 minutes.

Patient test serum (25 μl) was added to serum diluent (250 μl) and the mixture added dropwise through the window of the assay device onto the antigen-spotted nitrocellulose membrane. After the sample had completely soaked through the membrane, 300 μl of post-sample wash was added {50 mM Trizma-Base (Sigma), 2 M sodium chloride, 1% w/v TRITON X-705 (70% w/v solution, (Sigma), 0.2% w/v sodium azide, pH 8.0}a polyoxyethylene ethe surfactor.

Detection reagent (300 82 l) was added, followed by two increments of 300 82 l each of post-liposome wash (PBS, 0.5% TWEEN 20, a polyoxyethylenesorbitan surfactant and 0.2% w/v sodium azide pH 7.2). After the wash had soaked through the membrane, the window area of the device was observed. Appearance of a red to pink triangle indicates that the patient serum is positive for antibodies against *Borrelia burgdorferi*. If only a small red dot is present in the center of the window in the absence of a red or pink triangle, the patient is negative for those antibodies. (If no dot is seen, the test should be repeated.) The total elapsed time measured from application of the diluted test serum until color formation is about 1 ½ minutes.

EXAMPLE II

Comparison of Specificity With and Without Preadsorption

Seven serum samples from patients known to be Lyme negative but who showed rheumatoid symptoms were obtained from the New England Medical Center (NEMC), Boston, Ma. Three serum samples from asymptomatic Lyme negative patients were obtained from Roche Biomedical Laboratory (RBL), Burlington, N.C. These samples were assayed by the procedure of Example I with and without absorbing antigen from *A. cal.* and *T. phag.* The following results were obtained:

| SAMPLE NUMBER | SOURCE/ CODE | NO PRE-ADSORP-TION | A. cal. PRE-ADSORP-TION | T. phag. PRE-ADSORP-TION |
|---|---|---|---|---|
| 1 | RBL 24 | + | + | − |
| 2 | RBL 39 | + | +/− | − |
| 3 | RBL 40 | + | +/− | − |
| 4 | NEMC 106 | + | +/− | − |
| 5 | NEMC 100 | + | − | − |
| 6 | NEMC 122 | + | − | − |
| 7 | NEMC 124 | + | + | − |
| 8 | NEMC 139 | + | − | − |
| 9 | NEMC 186 | + | − | − |
| 10 | NEMC 188 | + | +/− | − |

Key
+ = Definite positive
− = Negative
+/− = Faint positive
−/+ = Very faint positive It is seen from the above data that all ten Lyme negative serum samples gave false positive results in the absence of preadsorption. In contrast, preadsorption with *A. cal* gave four negatives, two false positives and four faint false positives. Preadsorption with *T. phag.* converted all false positives to negatives.

EXAMPLE III

The assay of Example I was repeated using a serum pool from normal subjects, a pool from known Lyme positive patients and a pool of Lyme negative, false positive sera. This experiment included preadsorption with sonicated preparations of the following microorganisms closely related to *A. cal.*

The following results were obtained:

| ORGANISM | POSITIVE SERUM POOL | NEGATIVE SERUM POOL | FALSE POSITIVE SERUM POOL |
|---|---|---|---|
| NONE (CONTROL) | + | −/+ | +/− |
| A. cal. var. anitratus | + | − | − |
| T. phag. | + | − | − |
| A. cal. var. iwoffi | not done | − | + |
| Oligella urethralis | + | −/+ | + |
| Moraxella phenylpyruvica | + | −/+ | + |
| Moraxella osloensis | + | − | + |
| Flavobacterium odoratum | + | − | + |
| Flavobacterium meningosepticum | + | +/− | + |
| Flavobacterium breve | + | +/− | + |

It is seen that only *A. cal.* and T. phag. eliminated the false positives.

EXAMPLE IV

The assay of Example I was repeated using a serum pool from known Lyme positive patients, a pool from normal subjects and a pool of Lyme negative false positive sera. This experiment was carried out with preadsorption of the sera with sonicated, lyophilized and reconstituted *T. phag.* and with unsonicated (intact) *T. phag.* cells. The following results were obtained:

| | PREADSORPTION WITH T. phag. | |
|---|---|---|
| SAMPLE | Unsonicated | Sonicated |
| Lyme positive | + | + |
| Normal | − | − |
| False positive | − | − |

This experiment shows that either disrupted cells or intact cells may be used for preadsorption of crossreactive antibodies.

What is claimed is:

1. A method of assay for anti-Borrelia burgdorferi antibodies in a serum sample comprising:
   a) preparing a mixture of the serum sample and an Acinetobacter calcoaceticus absorbing antigen such that cross-reacting antibodies in the sample bind to the absorbing antigen;
   b) passing the mixture through a porous membrane coated with a Borrelia burgdorferi capture antigen such that the anti-Borrelia burgdorferi antibodies bind to the capture antigen on the membrane and the cross-reacting antibodies bound to the absorbing antigen do not substantially bind to the capture antigen;
   c) contacting the bound anti-Borrelia burgdorferi antibodies with a detection antibody conjugated to a liposome encapsulating an absorbing dye such that the detection antibody binds to the anti-Borrelia burgdorferi antibodies bound to the capture antigen; and
   d) detecting the presence of the anti-Borrelia burgdorferi antibodies by detecting the dye on the membrane.

2. A method of assay for anti-Borrelia burgdorferi antibodies in a serum sample comprising:
   a) preparing a mixture of the serum sample and an Acinetobacter calcoaceticus absorbing antigen such that cross-reacting antibodies in the sample bind to the absorbing antigen;
   b) passing the mixture through a porous membrane coated with a Borrelia burgdorferi capture antigen such that the anti-Borrelia burgdorferi antibodies bind to the capture antigen on the membrane and the cross-reacting antibodies bound to the absorbing antigen do not substantially bind to the capture antigen;
   c) contacting the bound anti-Borrelia burgdorferi antibodies with a detection antibody conjugated to a dye such that the detection antibody binds to the anti-Borrelia burgdorferi antibodies bound to the capture antigen, and;
   d) detecting the presence of the anti-Borrelia burgdorferi antibodies by detecting the dye on the membrane.

3. A method of assay for anti-Borrelia burgdorferi antibodies in a serum sample comprising:
   a) preparing a mixture of the serum sample and an Acinetobacter calcoaceticus absorbing antigen such that cross-reacting antibodies in the sample bind to the absorbing antigen;
   b) contacting the mixture with a solid support coated with a Borrelia burgdorferi capture antigen such that the anti-Borrelia burgdorferi antibodies bind to the capture antigen on the solid support and the cross-reacting antibodies bound to the absorbing antigen do not substantially bind to the capture antigen;
   c) contacting the bound anti-Borrelia burgdorferi antibodies with a detection antibody conjugated to a dye such that the detection antibody binds to the anti-Borrelia burgdorferi antibodies bound to the capture antigen; and;
   d) detecting the presence of the anti-Borrelia burgdorferi antibodies by detecting the dye on the membrane.

4. A kit of materials for performing an assay for anti-Borrelia burgdorferi antibody in a serum sample comprising:
   a) an enclosure;
   b) a filter stack in the enclosure, the filter stack including a porous membrane and a pad of absorbent material in contact with the membrane, the membrane having thereon a coating of Borrelia burgdorferi capture antigen;
   c) an Acinetobacter calcoaceticus absorbing antigen for absorbing cross-reacting antibodies in the serum sample, and;
   d) a tracer comprising a detection antibody labeled with a dye.

5. A kit of materials for performing an assay for anti-Borrelia burgdorferi antibody in a serum sample comprising:
   a) an enclosure;
   b) a filter stack in the enclosure, the filter stack including a porous membrane and a pad of absorbent material in contact with the membrane, the membrane having thereon a coating of Borrelia burgdorferi capture antigen;
   c) an Acinetobacter calcoaceticus absorbing antigen for absorbing cross-reacting antibodies in the serum sample, and;
   d) a tracer comprising an antihuman detection antibody conjugated to a liposome encapsulating an absorbing dye.

6. The method according to claims 1, 2 or 3 wherein the serum sample is mixed with an absorbing antigen comprising intact microbial cells.

7. The method according to claims 1, 2 or 3 wherein the serum sample is mixed with an absorbing antigen comprising a sonicate of microbial cells.

8. The method according to claims 1, 2 or 3 wherein the bound antibodies are contacted with a detection antibody comprising an anti-human antibody.

9. The method according to claims 2 or 3 wherein the boudn antibodies are contacted with a detection antibody conjugated to a dye selected from the group consisting of fluorescent dyes and absorbing dyes.

10. The method according to claim 1 wherein the bound antibodies are contacted with a detection antibody conjugated to a liposome encapsulating a dye selected from the group consisting of fluorescent dyes and absorbing dyes.

11. The method according to claim 2 wherein the membrane is further coated with an inert protein.

12. The kit according to claim 4 or 5 wherein the absorbing antigen comprises intact microbial cells.

13. The kit according to cliam 4 or 5 wherein the absorbing antigen comprises a sonicate of microbial cells.

14. The kit according to claim 4 or 5 wherein the detection antibody is an anti-human antibody.

15. The kit according to claim 4 or 5 wherein the dye is selected from the group consisting of fluorescent dyes and absorbing dyes.

* * * * *